(12) United States Patent
Marshall

(10) Patent No.: US 6,425,880 B1
(45) Date of Patent: Jul. 30, 2002

(54) MEDICAL SYRINGES

(75) Inventor: Jeremy Marshall, Jericho (GB)

(73) Assignee: Owen Mumford Limited, Oxford (GB)

( * ) Notice: Subject to any disclaimer, the term of this patent is extended or adjusted under 35 U.S.C. 154(b) by 0 days.

(21) Appl. No.: 09/743,608

(22) PCT Filed: May 11, 2000

(86) PCT No.: PCT/GB00/01811

§ 371 (c)(1),
(2), (4) Date: Mar. 14, 2001

(87) PCT Pub. No.: WO00/69494

PCT Pub. Date: Nov. 23, 2000

(30) Foreign Application Priority Data

May 12, 1999 (GB) .............................................. 9910865

(51) Int. Cl.⁷ ............................................. A61M 37/00
(52) U.S. Cl. ....................................................... 604/82
(58) Field of Search ............................ 604/82, 84, 110, 604/191, 192, 198, 232, 234

(56) References Cited

U.S. PATENT DOCUMENTS 4,642,103 A * 2/1987 Gettig ........................ 604/234
4,743,229 A * 5/1988 Chu ............................. 604/82
5,472,022 A * 12/1995 Michel et al. ................. 604/82
5,775,506 A * 7/1998 Grabenkort .................. 604/232

FOREIGN PATENT DOCUMENTS

| WO | WO 97/07839 | 3/1997 |
| WO | WO 98/57734 | 12/1998 |
| WO | WO 00/13723 | 3/2000 |

* cited by examiner

*Primary Examiner*—Anhtuan T. Nguyen
(74) *Attorney, Agent, or Firm*—Young & Thompson

(57) ABSTRACT

A syringe (1) contains a liquid medical substance which has to be mixed with another substance before use. This is done by interconnecting the syringe (1) and a capsule containing the other substance by a transfer device (2) which screws into a socket (4) in the piston-seal (3) of the syringe (1) and penetrates through into the liquid. The device (2) extends slidably but non-rotatably through a screw cap (8) which fits to the rear end of a housing (13) for the syringe (1). As the cap (8) screws on, so does the transfer device (2) screw into the piston-seal (3). The relationship between the screw threads is such that, on removing the screw cap (8), the transfer device (2) disengages from the piston-seal (3) first, so that the latter cannot be inadvertently removed from the syringe.

3 Claims, 1 Drawing Sheet

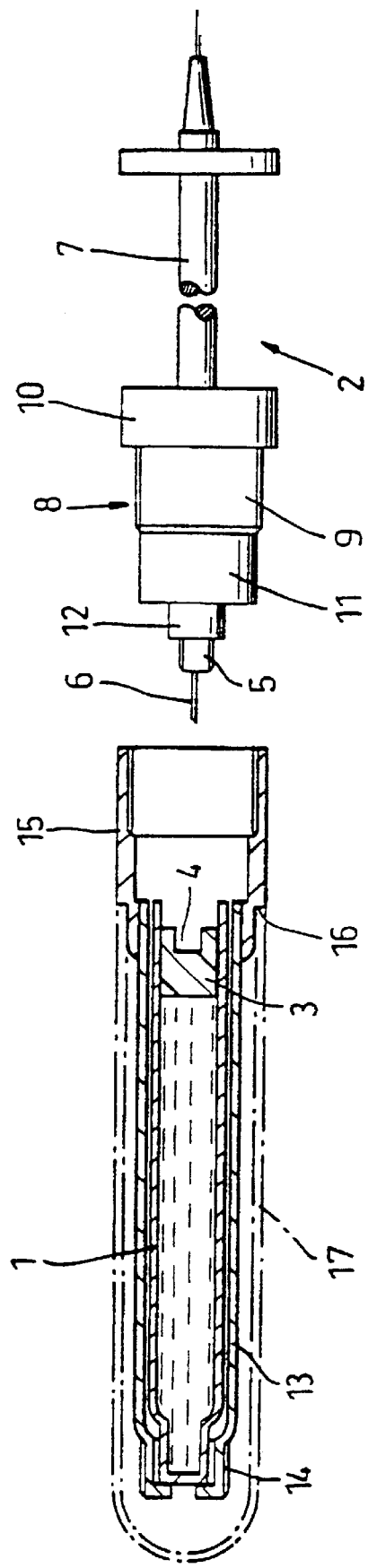

MEDICAL SYRINGES

This invention relates to medical syringes. It is concerned with those where a liquid part of a medical substance is initially kept in a syringe while another part, which may be in liquid or powder form, is in a separate capsule. A transfer device couples the syringe and capsule, and in a preliminary operation the liquid in the syringe is conveyed through its piston-seal to the capsule, where it mixes with the contents, and then back in ready-to-use mixed form to the syringe. The transfer device is decoupled, and a piston rod can then be fitted to the piston seal.

Various arrangements are described in WO 00/13723. However, there is a risk, at the end of the transfer process and when decoupling the transfer device from the syringe, of pulling out the piston seal, and it is the aim of this invention to reduce or possibly eliminate that risk.

According to the present invention there is provided a syringe assembly comprising a syringe with a first liquid medical substance and a transfer device connectable thereto for preparatory mixing of said first substance with a second medical substance in a capsule connectable elsewhere to the transfer device, the syringe having a piston-seal with a screw-threaded socket facing rearwardly to the open end of the syringe, and the transfer device having a needle projecting from its leading end which screws into said recess while the needle penetrates through the piston-seal into the first substance, wherein a cap is slidable axially up to a forward limit but is non-rotatable with respect to the transfer device which extends co-axially through it, and wherein the cap has screw-threaded engagement with the rear end of the syringe, the arrangement being such that, when the transfer device is offered up to the syringe and the cap at its forward limit is screwed thereto, the transfer device, rotating with the cap, screws into the piston-seal and completes its attachment thereto before the completion of the cap and syringe attachment, and such that the removal of the transfer device is by unscrewing the cap, which frees the transfer device from its engagement with the screw-threaded socket before the cap is freed from the syringe.

Generally, the syringe will have a capsule within a housing with which it is effectively integral, and it is the housing which will have the screw thread for engagement by the cap. In that case, the cap may penetrate into the rear end of the housing and, when screwed fully home, engage the rear end of the capsule to clamp that firmly within the housing.

The pitch of the screw threads may be such that both the cap and the transfer device move forward together in unison. But the axial length of the thread in the socket will then be shorter than the axial length of the cap thread. Alternatively, the socket may have a thread of relatively coarse pitch compared with that of the cap, so that the transfer device advances ahead of the cap until it is fully home in the piston-seal socket. The cap continues to be screwed on, and "catches up" the transfer device.

For a better understanding of the invention, one embodiment will now be described, by way of example, with reference to the accompanying drawing in which the single figure is an exploded view, partially in axial section, of a transfer device and syringe.

A syringe capsule 1 and a transfer device 2 are substantially as described in WO 00/13723. The capsule 1 contains a liquid medical substance confined by a piston-seal 3 with a central socket 4 in its exposed rear side into which screws the threaded leading end portion or nose 5 of the transfer device. This causes a needle 6 projecting from the nose to penetrate through the piston-seal 3 into the liquid. The needle 6 is hollow and communicates with a transfer canal within the device 2. A second capsule (not shown) with another medical substance to be mixed with the liquid will be fitted to the other end of the transfer device.

At the end of the procedure for preparing the contents of the syringe, the needle 6 has to be withdrawn from the piston-seal 3, the transfer device 2 being replaced by a piston rod to eject the dose. It has been found that there is a danger that, instead of a careful unscrewing action, the syringe and the transfer device can be inadvertently pulled apart before the threads are disengaged, and this plucks the piston-seal 3 out of the syringe, with disastrous results. There is also a risk of retracting the piston-seal too far towards the end of the transfer process, when the mixed dose is being pulled back into the syringe from the capsule at the other end of the transfer device.

To prevent this, the stem 7 of the transfer device 2 passes through a screw cap 8. It can slide longitudinally with respect to the cap but being of non-circular section, it cannot rotate. An externally screw-threaded portion 9 is forward of an enlarged disc-like head 10, and a plain cylindrical section 11 continues beyond the screw thread. The stem 7 has an annular enlargement 12 immediately behind the nose 5 which is an easy fit into the syringe capsule and which acts as a stop limiting the forward movement of the cap 8 relative to the transfer device.

The capsule 1 locates in a tubular housing 13, its forward end seating in an externally screw threaded neck 14 which will receive a needle assembly (not shown) Conveniently, the housing is transparent, and is marked with a scale to indicate the dose in the capsule 1. At its rear, open end, it is provided with a collar 15 internally screw threaded to receive the cap 8. Externally the collar reduces at a forward facing shoulder 16, and over this lesser diameter portion a casing 17, indicated in broken lines, can snap-fit.

When the coupling element 2 is offered up, the needle 6 enters the socket 4 of the piston-seal 3, which is near the rear end of the filled syringe. The cap 8 is slid forwards along the stem 7 until it meets the enlargement 12 and is screwed into the collar 15. As this happens, so will the nose 5 engage the socket 4 and screw into that. The screw threaded portion 9 is considerably longer than the portion 5, which ensures that the latter is fully home in the piston-seal 3 before the head 10 meets the rear end face of the collar 15. Over the last few turns of the cap 8, the piston-seal 3 will rotate and advance a short distance, and as the cap seats so the end of the portion 11 comes to bear firmly on the rear end of the syringe capsule 1 and clamp it in position in the housing 13. The small forward movement of the piston-seal 3 causes some of the liquid in the capsule 1, into which the hollow needle 6 has now penetrated, to flow into the canal through the transfer device 2 and possibly reach the capsule at the other end. The rest of the liquid follows during the transfer and mixing process. With the cap 8 in place, there is no chance of the piston-seal 3 escaping.

When the time comes to disengage the transfer device 2, the cap 8 has to be unscrewed. This action also unscrews the nose S from the piston-seal 3, and again because of the relative lengths of the screw threaded portions, the piston-seal 3 is disengaged before the cap B is clear of the collar 15. Therefore, when the transfer device 2 is pulled clear, the piston-seal 3 will be left safely behind in the syringe 1.

What is claimed is:

1. A syringe assembly comprising a syringe with a first liquid medical substance and a transfer device connectable thereto for preparatory mixing of said first substance with a second medical substance in a capsule connectable elsewhere to the transfer device, the syringe having a piston-seal with a screw-threaded socket facing rearwardly to the open end of the syringe, and the transfer device having a needle projecting from its leading end which screw into said recess while the needle penetrates through the piston-seal into the first substance, wherein a cap is slidable axially up to a forward limit but is non-rotatable with respect to the transfer device which extends co-axially through it, and wherein the cap has screw-threaded engagement with the rear end of the syringe, the arrangement being such that, when the transfer device is offered up to the syringe and the cap at its forward limit is screwed thereto, the transfer device, rotating with the cap, screws into the piston-seal and completes its attachment thereto before the completion of the cap and syringe attachment, and such that the removal of the transfer device is by unscrewing the cap, which frees the transfer device from its engagement with the screw-threaded socket before the cap is freed from the syringe.

2. A syringe assembly as claimed in claim 1, wherein the syringe has a capsule within a housing with which it is effectively integral, and it is the housing which has the screw thread for engagement by the cap.

3. A syringe assembly as claimed in claim 2, wherein the cap penetrates into the rear end of the housing and, when screwed fully home, engages the rear end of the capsule to clamp that firmly within the housing.

* * * * *